US00PP09788P

United States Patent [19]

Grant et al.

[11] Patent Number: Plant 9,788

[45] Date of Patent: Jan. 28, 1997

[54] SWEET GUM TREE NAMED 'GRANT'S SEEDLESS ZN-4'

[76] Inventors: William R. Grant; Elizabeth M. Grant; W. Cal Grant, all of 1018 Pawnee Rd., Wilmette, Ill. 60091

[21] Appl. No.: 521,243

[22] Filed: Aug. 31, 1995

[51] Int. Cl.[6] ..... A01H 5/00

[52] U.S. Cl. ..... Plt./51.1

[58] Field of Search ..... Plt./51.1

*Primary Examiner*—James R. Feyrer

[57] ABSTRACT

A new and distinct Sweet Gum tree named 'Grant's Seedless Zn-4', which is particularly characterized by its lack of fruits or seed pods, and its hardiness to minus 25 degrees Fahrenheit (USDA ZONE 4B), and, its canopy, which allows vigorous and healthy lawn growth and has intense Burgundy red and golden yellow Fall colors.

3 Drawing Sheets

BACKGROUND OF THE INVENTION

The present invention relates to a new and distinct tree of the species *Liquidambar styraciflua,* which is commonly known as the Sweet Gum Tree. We have called this new cultivar by the cultivar name 'Grant's Seedless Zn-4' in honor of Elizabeth May Grant's and William Calloway Grant's discovery and subsequent successful work on the asexual reproduction of the tree. It is anticipated that the tree will be sold under the trademark "Grants' Sunrise".

This new *Liquidambar styraciflua* tree was discovered in 1983 on the lawn surrounding our new home. On Dec. 24, 1983 the day's high temperature was −11 degrees below zero and the low was minus 23 degrees below zero Fahrenheit (USDA Zone 4b) at Glenview Naval air base (about 3 miles from the location of the tree). That spring we found the tree had not been affected by the extreme cold of that winter as there was more than one foot of new growth on its limbs; and we were also told it had not suffered any damage from the minus 26 degrees cold on Jan. 16, 1982. On Jan. 20, 1985, it survived, without damage, die-back or winter kill, a temperature of minus 31 degrees below zero (USDA Zone 3b) at Glenview and an official record low of minus 27 degrees below zero at the U.S. Weather station at O'Hare Airport, 15 miles south of the tree. We realized the tree was distinct from other *L. styraciflua* varieties as it did not suffer from the extreme cold of those winters, while similarly exposed trees of the same species were severely damaged or killed. On Jan. 18, 1994, this new cultivar and three of its successive generations created through grafting, also went through the extremes of cold of minus 26 degrees at the Glenview Naval Air base and minus 21 degrees below zero Fahrenheit at the U.S. Weather Station at O'Hare Airport. That spring's new growth of the cuttings that had been grafted onto three common Sweet Gum seedlings was 3 to 5 inches, with no signs of damage, die-back or winter kill on their branches (see FIGS. 4 and 7 of the drawing). One of the specimens of this tree was subsequently transplanted to the Lansing, Mich. area and survived the Michigan winter of 1994–95.

As the owner of the property and the tree with my wife, Carol McGregor Grant, we researched the Sweet Gum Tree, and were surprised to see it survive the winter of 1993's weather without damage. Still I was determined to cut it down and replace it with a Maple variety, as I did not want to put up with the one inch fruits typical of our estimated 20 to 25 year old Sweet Gum. Fortunately, my son, Cal and my daughter Elizabeth, convinced us that we should not "kill" the tree. We promised not to cut it down until the tree developed the pods/fruits typical of *L. styraciflua* and like the fruits on a Sweet Gum tree six houses distant (approximately 550 feet). By 1986, our tree still had not produced any fruits, even though the neighbor's apparently younger Sweet Gum tree, had produced hundreds of seed pods yearly while also suffering winter die-back. So our originally discovered specimen, saved from the chainsaw by my daughter and son, was thriving through the coldest northern Illinois winters, and each spring it would grow eighteen inches without producing any fruits.

By 1992, almost ten years later, we knew we had a new and distinct variety of Sweet gum, as our tree was both fruitless and hardy. Asexual propagation by grafting cuttings onto common Sweet Gum seedlings was done of our direction at the Morton Arboretum. We Planted three of the grafted seedlings on Jul. 15, 1992. on Jan. 18, 1994 the temperature was minus 26 at Glenview, and minus 21 degrees below zero officially at O'Hare (USDA Zone 4b). All three grafted trees survived without damage and their new growth that spring is illustrated by FIGS. 3 and 5. These asexually reproduced grafted seedlings have proven and demonstrated that they have the novel and distinctive characteristics of this new variety and that they are fixed and hold true under asexual propagation from generation to generation. In 1995, Cal and Elizabeth Grant continued the cultivar's development by grafting 5 more seedlings and by 13 rooted cuttings with a 40% and 25% success rate, respectively.

The two 'Moraine' Sweet Gum specimens planted a mile from our trees suffered extensive "die-back" from cold winters and, contrary to recent claims, they have produced seeds and fruits for the past two years. The 'Goldust' variety is not hardy, and does not have the same burgundy red to golden-yellow Fall colors nor the same canopy density when compared to the tree of this disclosure. The 'Rotundiloba' tree has red rounded leaf lobes, and is only hardy to Zone 6. The 'Palo Alto', 'Festival', and 'Burgundy' Sweet Gum trees have seeds, and a greater percentage of Red to Yellow fall color. Finally, unlike many other Sweet gum varieties, our tree also has a canopy that is less dense than usual, as evidenced by the healthy and vigorous growth of lawns underneath specimens of our tree.

BRIEF DESCRIPTION OF THE VARIOUS VIEWS OF THE DRAWING

Our new variety 'Grant's Seedless Zn-4' Sweet Gum tree is illustrated with the following photographs which were taken over a period of three years and illustrating various characteristics which help to distinguish this tree:

Figure 1:
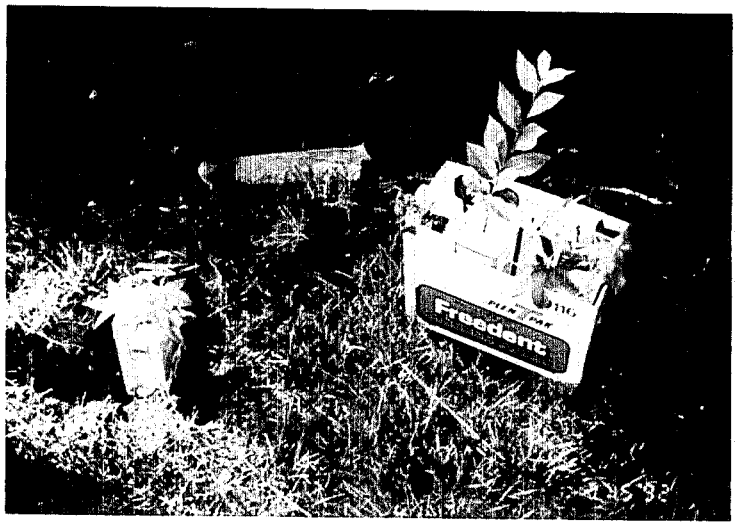
FIG. 1 shows cuttings from the originally discovered specimen of our tree which have been grafted onto three common *L. styraciflua* seedlings prior to planting in northern Illinois on Jul. 15, 1992. Shown as a reference to scale is a specimen of 'Don Alda' American Elm.
Figure 2:
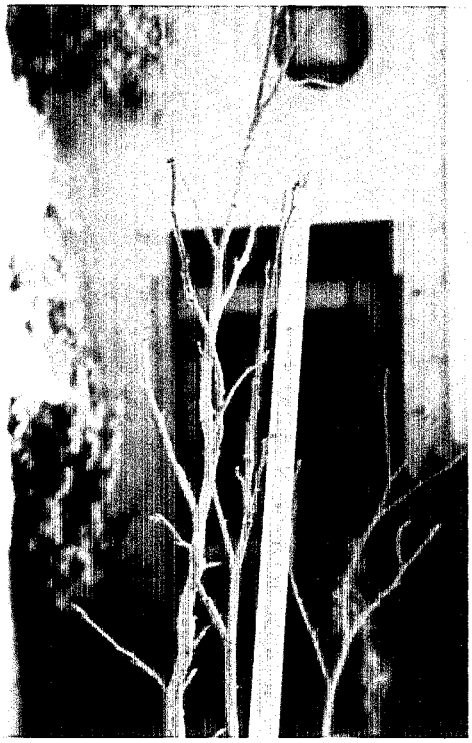
FIG. 2 depicts, in March 1994, the dormant terminal growth of the previous season on lower branches on the originally discovered tree.
Figure 3:
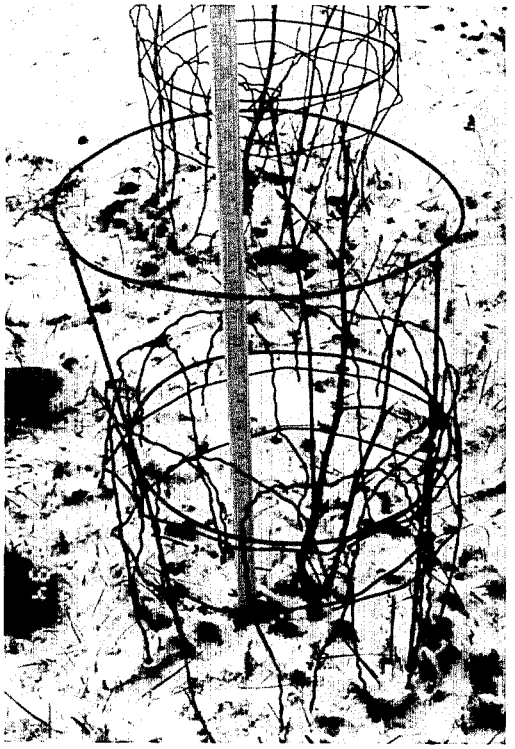
FIG. 3, illustrates two of the grafted specimens, in dormancy, showing the terminal growth of the previous season, during the winter of 1994 with weather of minus 26 degrees below zero. This photograph was taken on Mar. 11, 1994.
Figure 4:
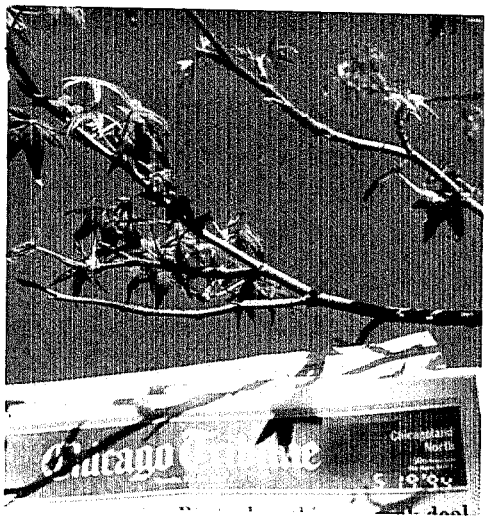
Figure 5:
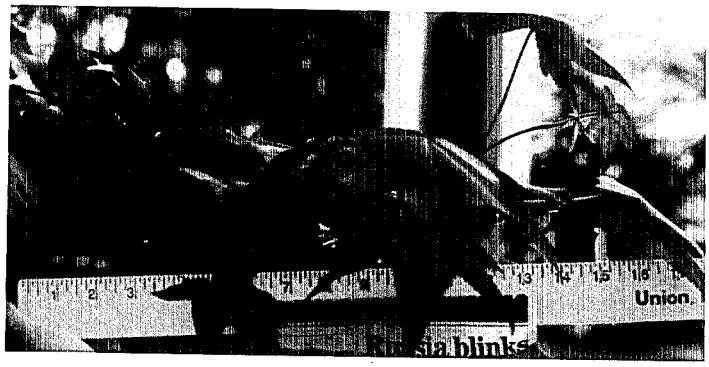

FIG. 4 shows the originally discovered specimen with the absence of fruit or seed with the new growth of 1994 after the winter of 1994, and the severely low temperature of minus 26 degrees. The photograph was taken on May 19, 1994. FIG. 5 is a close view of typical leaves in the terminal growth flush on the original specimen of the tree. This photograph was taken on Jun. 19, 1995.

Figure 6:
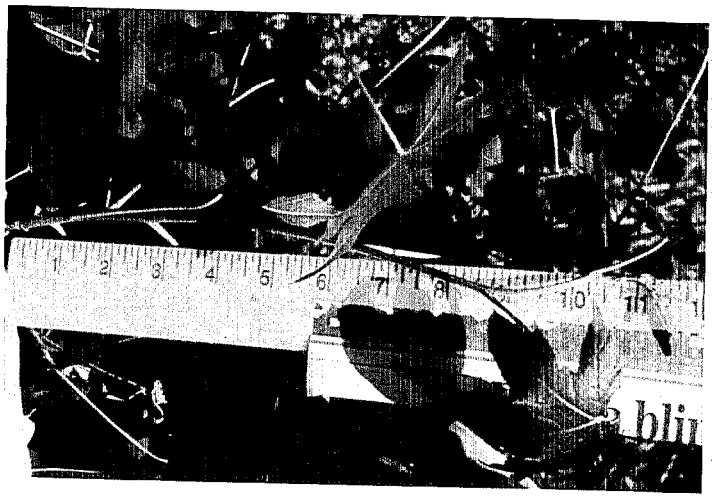

FIG. 6 shows new growth of a grafted specimen of our tree showing the terminal growth with the stem, internode length, petioles and foliage of 'Grant's Seedless Zn-4'.

Figure 7:
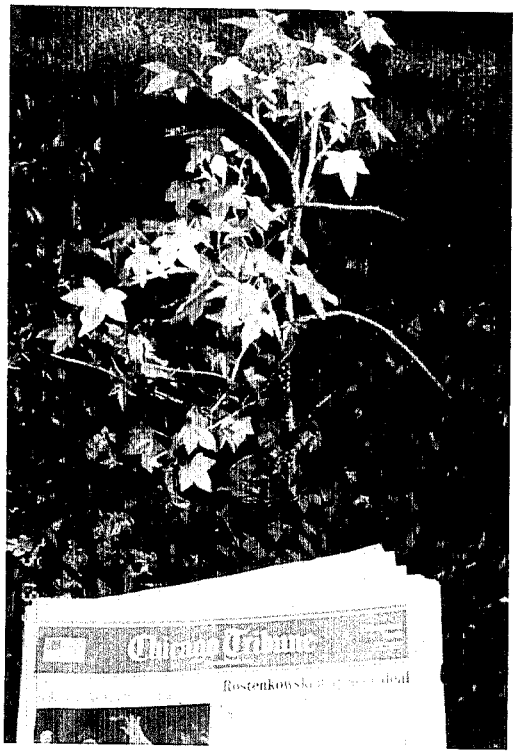

FIG. 7 depicts another specimen of our tree with a flush of growth after the severe winter of 1994. This photograph shows the early foliage coloration, maturing bark character as well as the early branching of a grafted specimen of the tree.

Figure 8:
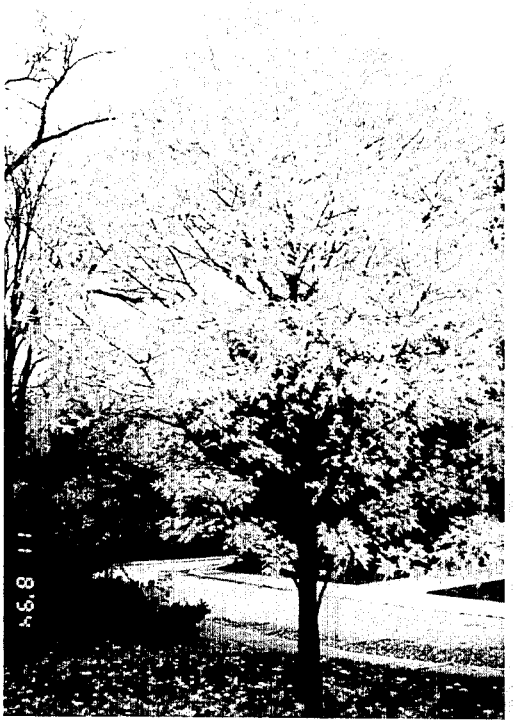

FIG. 8 is an illustration of a mature specimen of the tree which shows the attractive fall coloration of the tree just prior to leaf fall; and shows the more moderate canopy density of this tree and the strong branching habit of the tree.

Figure 9:
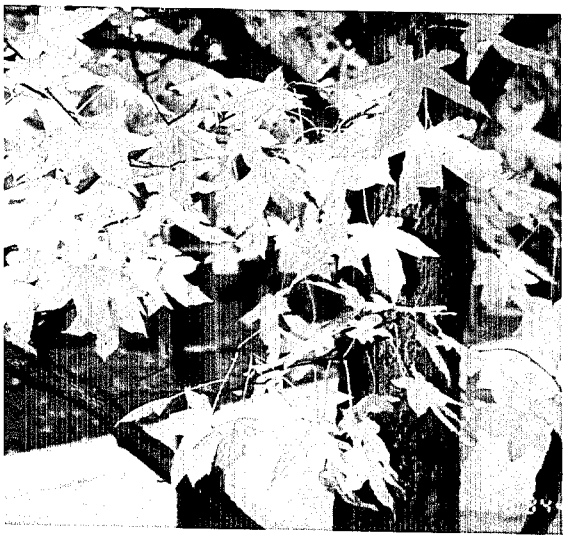

FIG. 9 is a close-up view of the fall coloration of our tree showing the lack of fruit, the details of bark character and color, texture, and the Burgundy-red to golden-yellow Fall colors of the foliage before leaf fall. This photograph was taken in 1994.

In the botanical description to follow, the color values of the various parts of this tree are defined with reference to *The Royal Horticulatural Society Colour Chart* except where color terms of ordinary meaning are clear.

BOTANICAL DESCRIPTION OF THE TREE

Name

*Botanical.*—*Liquidambar styraciflua.*

*Variety.*—'Grant' Seedless Zn-4'.

Parentage: Unknown, the tree of this disclosure was a random seedling within the species.

Strength: Hardy to at least 25 degrees Fahrenheit below zero and USDA Zone 4b. Strong limbs have withstood 50 mile per hour winds without major limb loss or breakage.

Tree shape: Upright and conical with spreading habit and a strong central leader, the scaffold branches are strong and strongly attached to the central leader. The canopy density is less than usual for most Sweet Gum varieties as evidenced by the vigorous and healthy growth of grass beneath the tree.

Height: Unknown as the oldest specimen is not full grown. It is anticipated that this tree will reach the full growth of the species, or about 75 feet, or more.

Bark: Thick, grayish-brown and with corky ridges on some branches, deeply furrowed into scaley ridges.

Petioles: 6 to 15 cm. long.

Buds: Ovoid to conical, pointed, glossy, reddish-brown.

Leaf color:

*Summer.*—RHS 137A. Fall — Burgundy Red in shades of RHS 45C, RHS 46A, and RHS 46B, with hues of red ranging from RHS 47B through RHS 47D; and red-purple RHS 59B.

*Fall.*—At leaf fall the predominant coloration is in shades of golden yellow RHS 14C; RHS 15B; RHS 21C RHS 22B and RHS 23C.

Leaves: Alternately arranged. simple, palmately lobed with five lobes, and long stalked, and same size and veings as in the species. Leaf lobes are oblong, triangular, toothed on the margins and pointed. Most lobes are not as wide as is typical for the species; with many center lobes only 5 to 7 cm wide while 12 to 14 cm long. Mature leaves are 22 to 28 cm wide and 15 to 20 cm long.

Flowers: No flowers have been observed at any time in the mature originally discovered specimen or any of the clonal progeny of this tree.

Bracts: No bracts have been observed at any time in the originally discovered tree or in any of the progeny of this tree produced by grafting.

Seeds: No seeds have been observed at any time in the mature originally discovered specimen of this tree, or in any of the asexally reproduced progeny of this tree and there is no reason to suspect that these will develop in the future. Numerous experts or artisans have been called upon to access the reasons for our tree's sterility but they have not come to a concensus as the cause of the sterility.

Fruit: No fruits have been observed at any time in the mature originally discovered specimen of this tree; nor in any of the grafted progeny of this tree and there is no reason to suspect that fruit will develop in the future as the tree and the grafted seedlings are sterile.

We claim:

1. A new and distinct variety of Sweet Gum tree, named 'Grant's Seedless Zn-4' as described and illustrated, and which is particularly characterized by its lack of fruits or seed pods, and its hardiness to minus 25 degrees Fahrenheit (USDA Zone 4b). and, its canopy, which allows vigorous and healthy lawn growth and has intense Burgundy red and golden yellow Fall colors.

* * * * *